United States Patent [19]

Tuckett et al.

[11] Patent Number: 5,363,859

[45] Date of Patent: * Nov. 15, 1994

[54] TACTILE TESTING DEVICE AND METHODS

[75] Inventors: Robert P. Tuckett; Kenneth W. Horch; John H. Fisher, all of Salt Lake City; Barry L. Evans, Murray, all of Utah

[73] Assignee: Topical Testing, Inc., Salt Lake City, Utah

[ * ] Notice: The portion of the term of this patent subsequent to Jun. 11, 2008 has been disclaimed.

[21] Appl. No.: 713,397

[22] Filed: Jun. 10, 1991

Related U.S. Application Data

[63] Continuation-in-part of Ser. No. 469,280, Jan. 24, 1990, Pat. No. 5,022,407.

[51] Int. Cl.$^5$ ................................................. A61B 5/00
[52] U.S. Cl. .................................... 128/739; 128/742; 128/744
[58] Field of Search ................ 128/736, 739, 740–742, 128/744, 630, 736, 739, 740–742, 744

[56] References Cited

U.S. PATENT DOCUMENTS

| | | | |
|---|---|---|---|
| 2,678,692 | 5/1954 | Ranseen | 128/630 X |
| 3,809,811 | 5/1974 | Delisle et al. | 179/1 N |
| 4,277,828 | 7/1981 | Tateishi | 364/415 |
| 4,299,230 | 11/1981 | Kubota | 128/630 |
| 4,306,291 | 12/1981 | Zilm et al. | 364/508 |
| 4,356,826 | 11/1982 | Kubota | 128/630 |
| 4,467,815 | 8/1984 | O'Brien et al. | 128/740 |
| 4,503,863 | 3/1985 | Katims | 128/741 |
| 4,641,661 | 2/1987 | Kalarickal | 128/744 |
| 4,653,507 | 3/1987 | Laudadio | 128/742 |
| 4,754,763 | 7/1988 | Doemland | 128/739 |
| 4,763,666 | 8/1988 | Strain et al. | 128/742 |
| 4,794,934 | 1/1989 | Motoyama et al. | 128/734 |
| 4,852,570 | 8/1989 | Levine | 128/630 |
| 4,940,060 | 7/1990 | Gu et al. | 128/735 |
| 5,002,065 | 3/1991 | LaCourse et al. | 128/739 |
| 5,022,407 | 6/1991 | Horch et al. | 128/739 |

FOREIGN PATENT DOCUMENTS 2583974 1/1987 France .

OTHER PUBLICATIONS

Chubbuck, J. G., "Small–Motion Biological Stimulator," APL Technical Digest, May–Jun. 1966.

Dyck, Peter J., M.D., et al., "Quantitation of Touch–Pressure Sensation," Arch. Neurol. vol. 26, May 1972.

Dyck, Peter James, M.D., et al., "Description of 'Minnesota Thermal Disks' and Normal Values of Cutaneous Thermal Discrimination in Man," Neurology, Apr. 1974.

Dyck, Peter James, M.D., et al., "Clinical vs Quantitative Evaluation of Cutaneous Sensation," Neurol., vol. 3, Sep. 1976.

Dyck, Peter James, M.D., et al., "Introduction of Automated Systems to Evaluate Touch–Pressure, Vibration, and Thermal Cutaneous Sensation in Man," Annals of Neurology, vol. 4, No. 6, Dec. 1978.

*Primary Examiner*—Lee S. Cohen
*Attorney, Agent, or Firm*—Madson & Metcalf

[57] ABSTRACT

An automatic apparatus for testing tactile responses of a patient is disclosed. The embodiments of the invention variously include components for: applying a nonambient temperature to the patient's skin to test the patient's response to thermal stimuli; pricking the patient's skin to test the patient's response to pain; indenting the patient's skin to test the patient's response to touch; vibrating the patient's skin to test the patient's response to vibration; and for making two spaced apart contacts with the patient's skin to test the patient's two point discrimination response. A general purpose computer and dedicated control circuits function to control the operation of the system and record the responses of the patient. The embodiments of the present invention are able to repeatedly reproduce each test so that the tests carried out are reproducible and accomplished in a minimum of time.

29 Claims, 14 Drawing Sheets

TACTILE TESTING DEVICE AND METHODS

RELATED APPLICATIONS

This application is a continuation-in-part of Applicant's copending application Ser. No. 07/469,280, filed Jan. 24, 1990, now U.S. Pat. No. 5,022,407 entitled "Apparatus and Method for Automated Tactile Testing," which application is incorporated herein by this reference.

BACKGROUND

1. The Field of the Invention

This invention relates to apparatus used to determine the response of a human patient to tactile stimulation. More particularly, the present invention relates to systems and methods for quantifiably determining a patient's responses to a variety of tactile stimuli in a repeatable and reproducible manner.

2. Technical Background

Many medical professionals and researchers need to determine a patient's response to various modes of tactile stimulus. For example, medical professionals dealing with the human nervous system often need to determine a patient's response to various tactile stimuli to assess the extent of any damage to the nervous system due to trauma or a degenerative condition.

Still further, rehabilitation and physical therapists concerned with monitoring a patient's progress during recovery from a head injury, stroke, or some other event affecting somatosensory function also must conduct tactile testing. Moreover, primary care providers often desire to perform tactile testing as a routine screening procedure for their patients but have been unable to do so because of the specialized training, equipment, and experience needed to perform tactile testing using existing methods.

It is now common for standard diagnostic tests to be used by neurologists, neurosurgeons, plastic and hand surgeons, and other surgeons to assess the functioning of a patient's nervous system. For example, in cases of central pathway lesion, differential loss of high versus low frequency vibration sense, temperature, and pain sensitivity is diagnostic of the pathways involved.

It is generally necessary to test all three of the principal modalities of cutaneous sensation, i.e., temperature, pain, and touch, in order to completely assess a patient's condition. Existing methods of testing the patient's thresholds and suprathresholds of temperature, pain, and touch involve manually applying the stimulus to the patient. Such manual methods are time consuming to prepare or administer, require a subjective determination by the administering technician, and are not consistently applied or reproducible from test to test.

For example, in order to test for pain using existing methods, a technician commonly jabs the patient with a sharp needle until a response is obtained. The manual jabbing of the patient with a needle requires that the technician be experienced at jabbing patients in order to avoid inflicting too much pain and drawing unnecessary blood. Still, regardless of the experience of the technician the use of the jabbing method does not result in quantifiable, objective, and reproducible results.

In the case of testing a patient's response to different temperatures, the conventional methods include having the patient touch vials or test tubes filled with liquids heated to varying temperatures. Aside from the difficulty of filling, heating, and maintaining the temperature of the vials or test tubes, the existing method is not well suited to testing the patient's tactile response to elevated temperatures on all areas of the body.

When measuring the patient's response to touch and vibration, various apparatus are used. Such apparatus include horse hairs and monofilament lines of varying thickness and stiffness which a technician presses against the patient's skin. Tuning forks are used to determine the patient's tactile threshold of sensing vibration.

In addition to the clinical application of tactile testing, neuroscience researchers interested in testing somatosensory function in man and other mammals routinely carry out tactile testing as part of their work.

In view of the foregoing, it would be an advancement in the art to provide a system and method to accurately and reproducibly test a patient's responses to one or more tactile stimuli. It would also be an advancement in the art to provide a system and method for automatically testing a patient's response to various modes of tactile stimulation which does not require special expertise to operate and maintains a record of the results of the testing. It would be a further advancement in the art to provide a system and method for automatically testing the tactile responses of a patient which imposes quantifiably accurate stimuli upon command and which carries out the testing in a relatively short period of time.

BRIEF SUMMARY AND OBJECTS OF THE INVENTION

In view of the foregoing, the present invention seeks to realize the following objects and advantages.

One primary object of the present invention is to provide a system and method to accurately and reproducibly test a patient's responses to one or more tactile stimuli.

Another important object of the present invention is to provide a system and method for automatically testing a patient's response to various modes of tactile stimulation which does not require special expertise to operate.

Another object of the present invention is to provide a system and method for automatically testing the tactile responses of a patient which imposes quantifiably accurate stimuli upon command.

It is another object of the present invention to provide a system and method for automatically testing the tactile responses of a patient which maintains a record of the results of the testing.

It is yet another object of the present invention to provide a system and method for automatically testing the tactile responses of a patient which carries out an array of tactile testing in a relatively short period of time.

These and other objects of the present invention will become more fully apparent during an examination of this disclosure and the appended claims and by practicing the invention.

In order to accomplish these and other objects, the present invention includes various tactile stimulation means for cutaneous stimulation of a patient. The embodiments of the invention comprise various tactile stimulation means including: temperature means for applying a nonambient temperature to the patient's skin; pinprick means for pricking the patient's skin; indentation means for indenting the patent's skin; vibration means for vibrating the patient's skin; touch discrimination means for making two spaced apart contacts with the patient's skin; and means for applying constant current stimuli.

A general purpose computer and dedicated control circuits function as the control means of the present invention in the embodiments described herein. The control means coordinates the operation of the various tactile stimulation means and in some embodiments includes means for recording the response of the patient.

The present invention is capable of automatically testing the three principal modalities of cutaneous sensation: temperature, pain and touch. The control means of the present invention provides for precise control of stimulus waveforms (temperature, force, current, indentation as a function of time, or current) so that reliable, quantitative data is obtained from the testing. The embodiments of the present invention are able to repeatedly reproduce each test waveform from a consistent initial condition and use predetermined sequences of stimuli so that the tests carried out are reproducible and accomplished in a minimum of time.

The method of operating the computer included in the control means minimizes the need for technical expertise on the part of the operating technicians and maximizes the present invention's flexibility by allowing new stimulus paradigms to be incorporated into the testing protocol by altering the programming code of the control means. This feature allows the embodiments of the present invention to modify the operation of the system in response to user requests or advances in the methodology of somatosensory testing by merely altering the programming code.

In addition, the present invention can be operated in such a manner that operator involvement is minimized. In particular, the present invention can be provided with means for allowing the patient to directly input responses to stimulation. For example, the patient may depress a button when he feels a stimulation, and then release the button when the stimulation is no longer felt. In another embodiment, the patient may position a slide to indicate the perceived intensity of the stimulus. The system is then capable of recording the input of the patient, and of producing subsequent stimuli in accordance with the stimuli.

The present invention can perform diagnostic clinical tests for which manual methods are inadequate, such as determining threshold values for sensing changes in vibratory frequency. The present invention also has application in research settings where testing to determine responses to cutaneous stimuli are important, such as in the study of peripheral nerve regeneration.

Because the present invention utilizes automated testing sequences and stimulus presentations, it takes less time to collect data for each patient. Furthermore, subjective problems such as observer bias and interactions between subject and technician are reduced or eliminated, particularly where the patient directly inputs signals in response to stimuli.

Since the present invention may be operated by a technician with only little experience with the system, the surgeon or other medical practitioner is freed from performing a task that may become a routine. It is only necessary that a standardized procedure be carried out by a technician. This ease of use of the system facilitates periodic retesting of patients, retesting being a prerequisite for properly evaluating the course of disease or a patient's recovery after undergoing a procedure.

DETAILED DESCRIPTION OF THE PREFERRED EMBODIMENT

Reference will now be made to the drawings wherein like structures will be provided with like reference designations.

Figure 1:
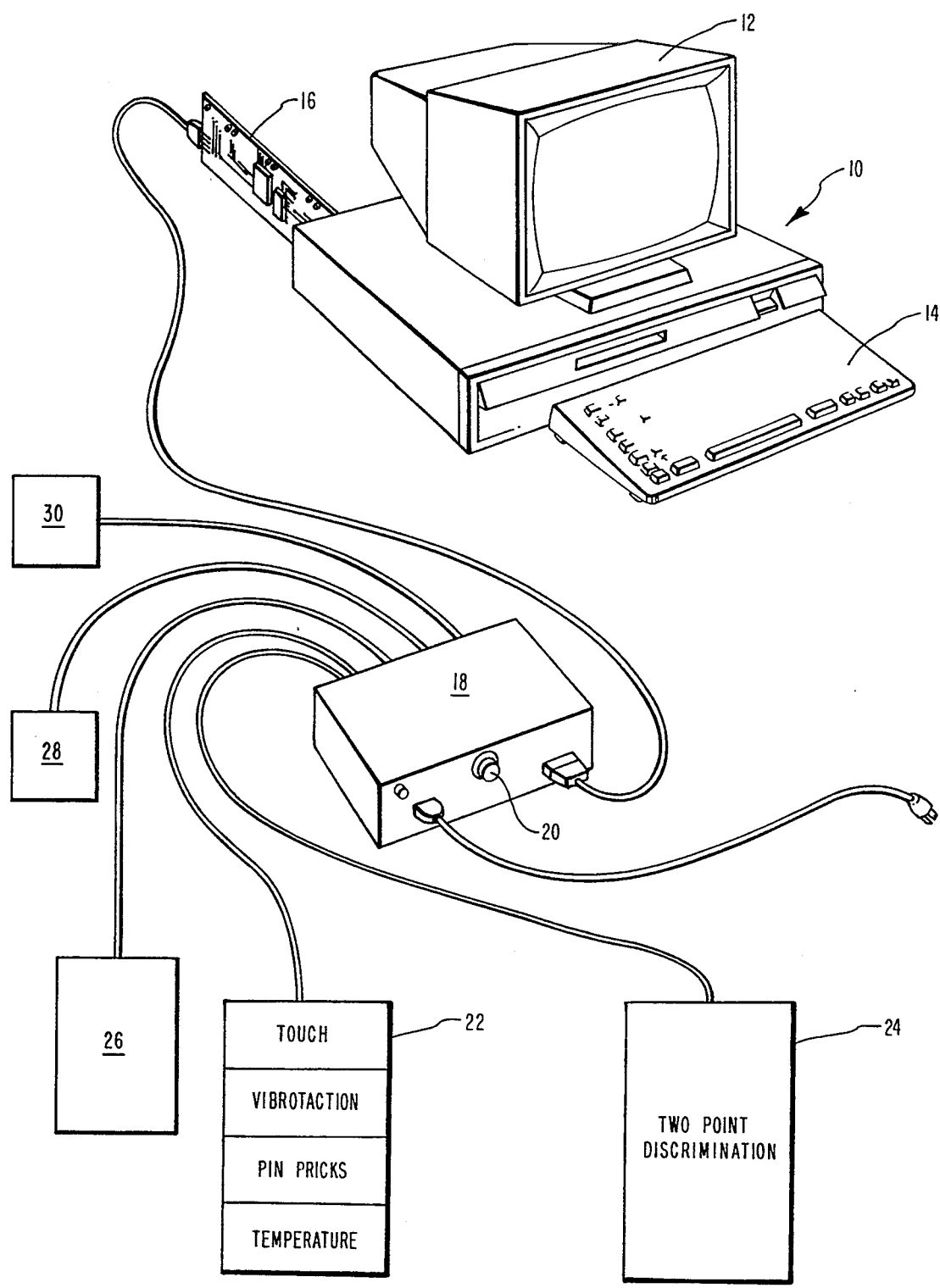
FIG. 1 is an overall view of one embodiment of the present invention.

Referring first to FIG. 1, an overall view of the presently preferred embodiment of the system of the present invention is provided. Represented in FIG. 1 is a microcomputer, generally designated at 10, which is preferably is equivalent to an International Business Machines (IBM) Model PC/XT or PC/AT microcomputer with a minimum of 128 Kilobytes of main memory. It will be appreciated that numerous computers are commercially available which are capable of performing the indicated functions. Accompanying the microcomputer 10 is a display 12 and a keyboard 14. These items are also commercially available in the art.

Also represented in FIG. 1 is a parallel expansion board 16. The parallel expansion board 16 provides an 8-bit digital-to-analog (D/A) converter and a parallel input-output port to interface between the computer 10 and the dedicated electrical circuits of the control module 18 which will be explained later. The parallel expansion board is commercially available and may comprise a board manufactured by the Qua Tech Company of Akron, Ohio, which is referred as model PBX-721, accompanied by a digital to analog converter module referred to as model DMS-10.

It will be appreciated that the computer and the control module 18 may be placed in communication by other methods known in the computer art. For example, the computer and the control module 18 may be placed in communication by way of an RS232 port in such a manner that the data acquisition card need not be placed within the computer. Rather, the board may be placed with the control module 18, and control module 18 may then be connected directly into a standard port in the back of the computer. Thus, an operator who is not particularly familiar with computer hardware is capable of easily connecting the necessary components. In addition, using this type of mechanism avoids possible damage to the various electrical components of the computer and the board.

It will be appreciated that while the just described components are preferred for use in the described embodiment, other components may be used in the place thereof in accordance with the teachings contained herein.

The control module 18 represented in FIG. 1 contains the dedicated electrical circuitry necessary to drive and control the stimulation producing components contained in the stimulation modules represented at 22, 24, and 26. In the illustrated system, the control module 18 preferably comprises a power supply, a printed circuit board containing a 2.5 KHz clock, logic circuits, buffer amplifiers, and feedback controlled power amplifiers for the stimulation imposing components which will be described in detail below.

The control module 18 is provided with a stimulus indicator 20 which indicates to the operating technician (represented in FIG. 2) when the stimulus is being imposed on a patient. While it is not required to separate the stimulation producing components into separate stimulation modules, with dedicated electrical circuitry in the control module, this configuration is illustrated in the illustrated embodiments.

As illustrated in FIG. 1, the first stimulation module 22 includes the components to carry out four stimulation functions: touch; vibrotaction; pinprick; and temperature. The second stimulation module 24 includes the components to carry out two point discrimination stimulation. The third stimulation module 26 includes the components necessary to generate constant current stimuli.

It will be appreciated that the functions contained within the various modules may vary, and the number of modules may also vary. In addition, other modules with other functions may also be substituted or added as desired. However, for purposes of illustration, three modules will be discussed in further detail. The components contained in each of the stimulation modules will be explained in detail below.

FIG. 1 also illustrates two monitors 28 and 30. These monitors may be provided with automatic means for the input of data from the patient. That is, the monitors either measure directly patient response, or allow the patient to input a response directly into the system. Again, these monitors will be discussed in further detail below.

Figure 2:
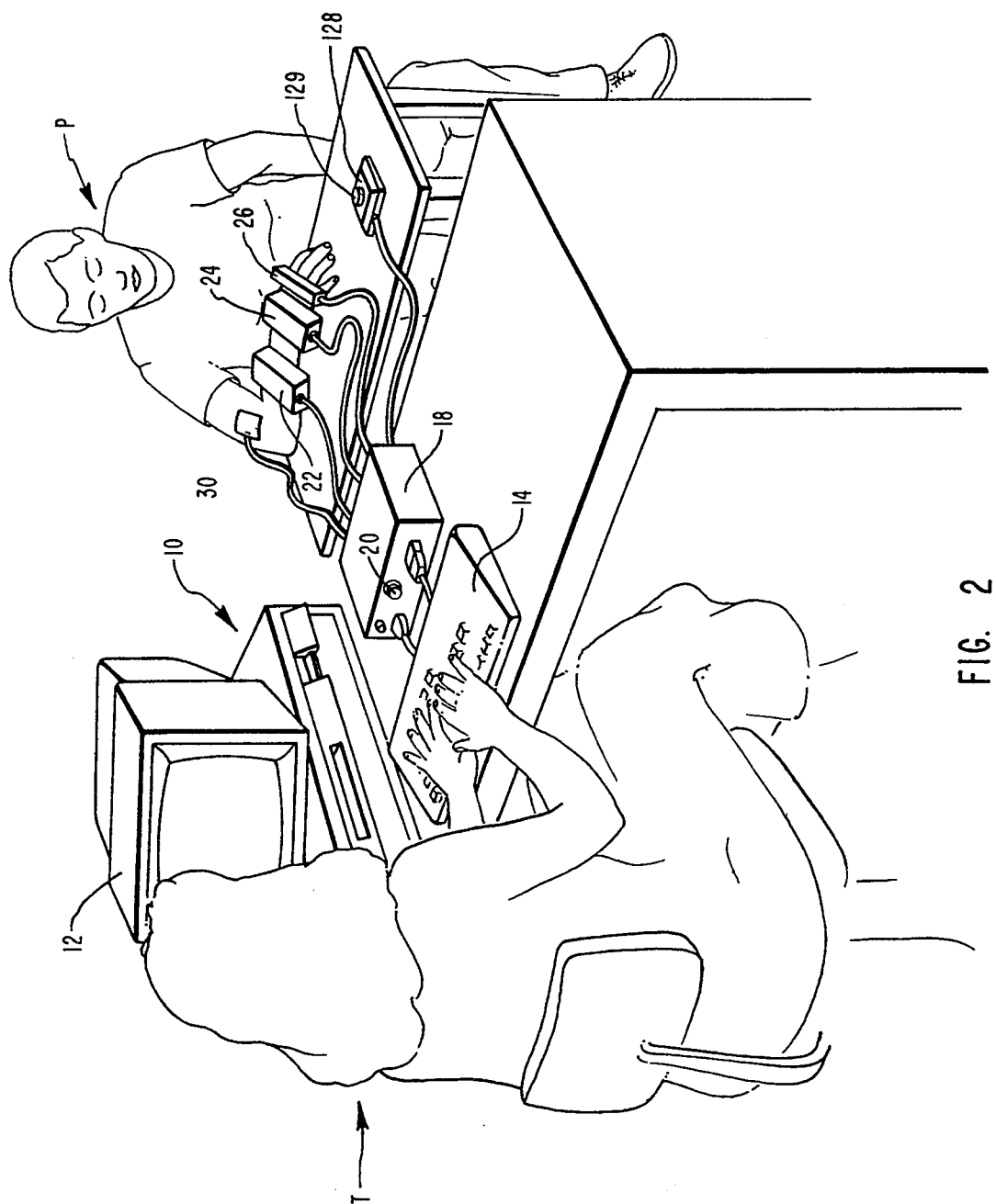
FIG. 2 illustrates one embodiment of the system of the present invention being used to test the tactile responses of a patient.

FIG. 2 provides an overall view of the system of the present invention in use. Represented in FIG. 2 is the microcomputer 10, control module 18 and first, second, and third stimulation modules, 22, 24 and 26 respectively, being operated by a technician T to test the tactile response of a patient or subject P. While the stimulation modules are shown positioned on the patient's arm, it will be appreciated that the stimulation modules 22, 24 and 26 may be positioned anywhere on the patient's body. For example, the stimulation modules can be held by the technician while the tests are carried out. Moreover, the configuration of the stimulation modules 22, 24, and 26 may be altered to be particularly adapted for use on a specific body part or for a specific clinical or research application.

Also illustrated in FIG. 2 are two monitors 128 and 30. Monitor 128 is positioned such that the patient can input responses. Monitor 30 is positioned directly on the patient in order to directly monitor physiological or electrical changes in the patient.

The stimulus indicator 20 illuminates when the stimulus is imposed upon the patient P. In the illustrated embodiment, the technician T observes the patient and determines whether the stimulus was perceived by the patient P. The stimulation indicator 20 signals to the technician (or alternatively to the patient) when the stimulus is imposed.

As has been mentioned above, it is also within the scope of the present invention to allow the patient to input directly to the system when a stimulus is perceived. This can be accomplished in a number of ways. For example, monitor 128 may include a button 129. In one embodiment of the invention, the button 129 is depressed by the patient P during the time that a sensory stimulus is felt. That is, as the stimulus is applied, the patient depresses the button 129 as soon as the stimulus is felt. The patient continues to depress the button 129 until such time as the stimulus is no longer felt. Feedback is provided to the system concerning the time period over which the stimulus is felt by the patient. This data can then be analyzed by means of the computer 10 and compared to the stimulus applied.

The monitor 128 and button 129 can be used to significantly automate the system. Since the response of the patient can be recorded directly by the system, it is possible to administer a series of tests and record the responses of the patient without constant input from a technician. For example, it will be possible for a physician to teach the patient how to depress the button 129 when a stimulus is felt. Then the system can be programmed to cycle through the desired series of tests. Since the patient's responses are automatically recorded by the system, the physician is provided with a full set of data, while minimizing the expense of technician or physician time.

In an alternative embodiment, the monitor 28 may comprise an LED display and a corresponding slide mechanism. The patient moves the slide mechanism along the display in proportion to the perceived stimulus. Again, the patient response (i.e. positioning of the slide) is recorded and correlated with the corresponding stimulus. Thus, direct patient input into the system is provided.

In still a further embodiment of monitor 28 it to directly monitor "finger span," such as the distance between the thumb and forefinger of the patient. The patient can extent this distance to indicate increased stimulus. The patient can also reduce the distance to indicate decreased stimulus. The distance of the span is constantly monitored and this data is feed back to the computer.

Thus, it can be seen that numerous mechanism exists for direct patient interaction and for directly recording patient responses. The use of these mechanisms reduce the need for technician and physician interaction. They also provide for increased accuracy by the elimination of transcription errors and error in oral communication from the patient to the technician.

Using any of the mechanisms discussed above, it is possible to automatically cycle through a "staircase" procedure or any other predetermined set of stimuli. In the "staircase" procedure the computer administers repeated stimuli until the patient indicates that a particular stimulus is felt. At that point, the computer reduces the amplitude of the stimulus until the patient no longer feels the stimulus. Use of the monitor 28 greatly facilitates this procedure. The patient simply depresses the button 129, moves a slider, or responds in some other way, when the stimulus is first felt. When the stimulus is no longer felt, the patient again responds by releasing the button, moving a slider, or making other appropriate gesture.

The present invention automatically deals with many record keeping tasks which would otherwise be burdensome to the technician. Moreover, the present system's organization of the data recorded during a test allows the data to be manipulated in many desirable ways which would be impractical if the data were manually recorded.

For example, the system described herein can keep a permanent record of the data from multiple testing sessions for each patient and can provide graphical and tabular summaries of the performance of a given patient over time providing an objective measure of the patient's progress. As will be discussed below, it is possible to compare the data obtained with baseline data loaded onto the computer. Thus, the present invention provides for significant improvements in the ability of medical professionals to diagnose somatic neuropathy and monitor somatosensory neural function.

As mentioned above, it is also possible to provide the computer with certain baseline data against which the patient's response is compared. For example, normal data can be accumulated, as can representative data for various abnormal conditions. Such conditions may including, for example, old age, leprosy, nerve regeneration, artificial and replacement skin (such as that used in treating burn victims), and numerous other disease or abnormal conditions. Once the desired data is loaded onto the computer 10, it is possible to compare the data obtained by measuring the patient response with either a normal baseline, or a baseline which is representative of particular disease, injury, or degenerative conditions.

The baseline data can easily be updated as needed and loaded onto the computer from a disk or other computer input mechanism. For example, in a commercial embodiment, it may be desirable for the user to subscribe to regular updates of the baseline data. Accordingly, the accuracy and reliability of diagnosis is significantly enhanced by comparing patient response against constantly updated baseline data.

The operation of the system is generally carried out under the direction of programming code, an example of which is attached as Appendix A to application Ser. No. 07/469,280. That programming code is run on the microcomputer 10. Among the functions carried out during the operation of the system using the code hereto are:

1) Creation of new patient files;
2) Patient log in and log out;
3) Testing of touch threshold to indentation stimuli using a staircase procedure;
4) Testing of touch threshold to sinusoidal stimuli using a staircase procedure;
5) Testing of two point discrimination response using a staircase procedure;
6) Testing of temperature threshold using a staircase procedure;
7) Testing of pain threshold using a pinprick and staircase procedure;
8) Magnitude scaling with skin indentations;
9) Magnitude scaling with sinusoidal skin indentations;
10) Magnitude scaling of two-point separation;
11) Magnitude scaling of temperature;
12) Magnitude scaling of pain;
13) Constant current application;
14) Display of patient data for a given type of test over time in both tabular and graphical forms; and
15) Printing out tabular or graphical displays of patient performance:
16) Comparing data obtained with baseline measurements.

Furthermore, using the code, when a patient is tested for the first time, the technician creates a data file in which is stored the patient's name and an identification number. Each time a test is run on the patient, a record of the date, the test parameters and the patient's responses are appended to the file. Subsequently, the user may extract data from this file for analysis and graphical display or tabular summary. This information may be sent either to the display or to a printer (not shown) for a permanent written report on the patient's performance. This file is stored in ASCII format, so it may be reviewed, edited, or printed with any number of commercially available word processing programs. Using the code, the technician is also able to preprogram a sequence of tests, and execute this sequence automatically by calling up a file with the sequence and parameter information stored in it.

In one embodiment of the programming code, at the beginning of each test sequence the technician is presented with a menu from which the operation to be performed is selected. The parameters for each test are provided with default values, which the technician may accept or change as desired. The operator instructs the patient on the basic procedure to be followed, and initiates the test. Responses of the subject or patient are typed into the microcomputer 10 by the operator, as prompted on the display. Inappropriate entries are trapped, and the technician is requested to provide a valid response.

Other function and data may be added to the code as desired. For example, application of constant current stimuli can also be control in a similar manner. Comparing baseline date with data collected during test runs can also be completed by appropriate modification to the programming code and the input of appropriate data into computer 10.

Figure 3:
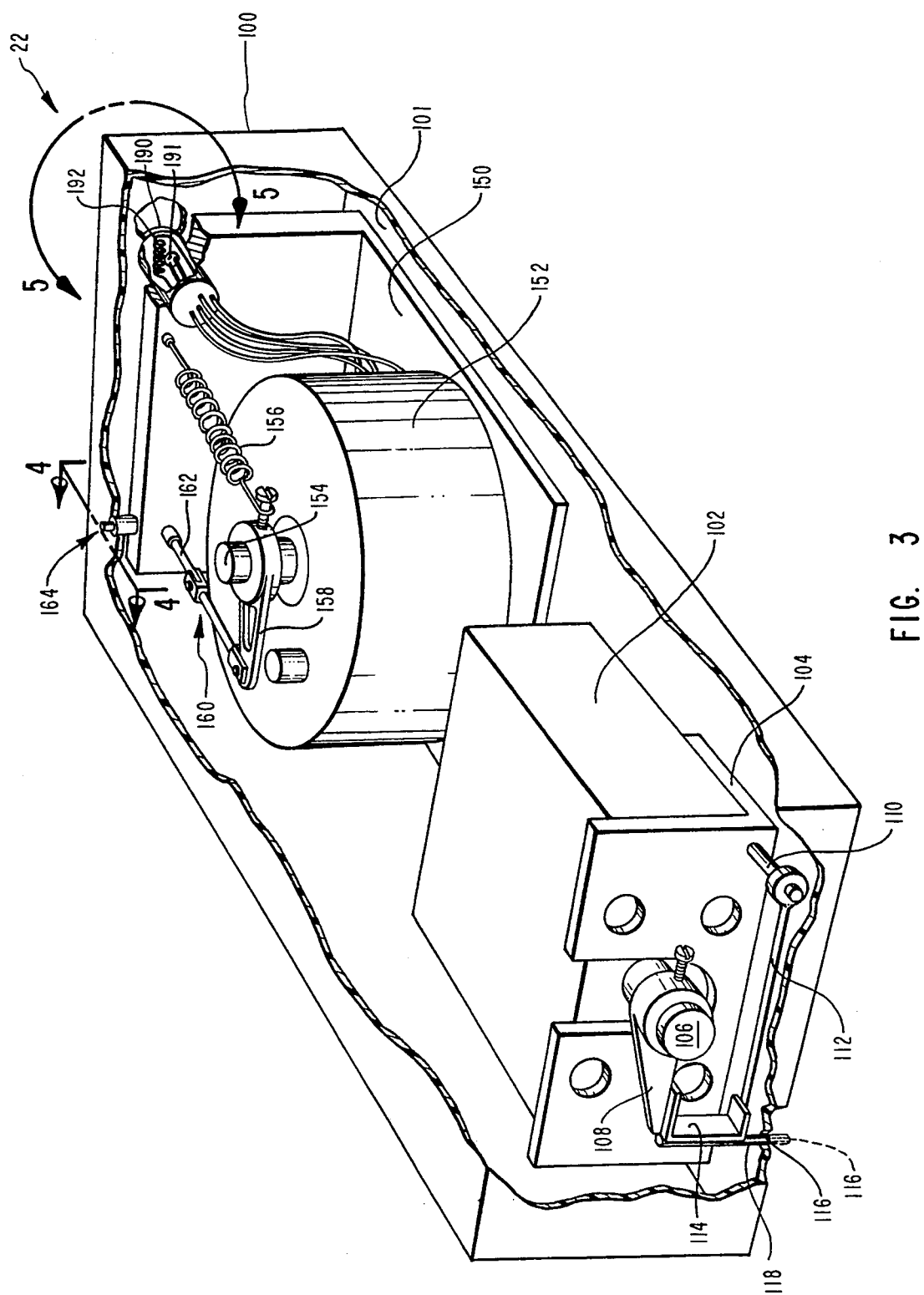
FIG. 3 is a partially cut away perspective view of one of the stimulator modules of the system of the present invention.

Referring next to FIG. 3, a partially cut away perspective view of one embodiment of the first stimulation module 22 which includes thermal stimulation means comprising an resistive heating element 192 with an embedded thermistor sensor 191. Also included in the first stimulation module is a pinprick stimulation means comprising a constant torque motor 152 (mounted to bracket 150) with a return spring 156 which is used for testing a patient's sensitivity to pinprick. Furthermore, the first stimulation module 22 includes a touch stimulation means and a vibrotaction stimulation means comprising a galvanometer 102 which moves a hex shaped rod 116 (shown fully retracted in solid image and fully extended in phantom image) to indent the skin of the patient.

As represented in FIG. 3, the components which carry out the touch and vibrotaction stimuli are particularly adapted for imposing the necessary stimuli upon the patient. Mechanical indentation to test touch and vibrotaction responses of the patient is produced by activating a galvanometer 102 (mounted on bracket 104). The preferred galvanometer 102 is available from General Scanning Inc. and referred to as model GVM620.

A brass lever arm 108 is attached to the galvanometer shaft 106. A plate 114, bent as shown in FIG. 3 and fabricated from 0.03 mm beryllium copper, is soldered onto the brass lever arm 108. The plate 114 is also soldered to another arm 112 which pivots about a hardened steel shaft 110. A nickel steel hex rod 116 is soldered to the plate 114. The hex rod 116 is provided with a blunt tip (1 mm diameter). Careful choice of the lever arm lengths allows the components to achieve a 1.2 mm maximum indentation with sufficient force to compensate for the compliance of the skin over soft tissues but with minimal lateral displacement of the blunt tip. If an attempt is made to indent the skin over, for example, a bony prominence, the embodiment limits the force imposed to a firm, but nonnoxious, pressure. The blunt tip is centered between the two sides of a 2 mm wide bore 118 in the base 101 of the housing 100.

In order to provide for precise control of small amplitude stimuli, the driving amplifier for the galvanometer 102 has a variable gain which is controlled by the computer as can be examined in a schematic diagram provided in a later figure. By selecting the proper gain based on the size of the indentation desired, the range of the 8-bit digital-to-analog converter included in the parallel expansion board 16 is increased by two orders of magnitude. Moreover, the use of galvanometer 102 allows the frequency of the vibration stimuli imposed on the patient's skin to be accurately controlled over a range of one or more hundred Hertz.

Various alternative embodiments are available for providing touch and vibrotaction stimuli. In particular, alternative devices could be mounted within the stimulus module 22. One such device is the Model 203B shaker manufactured by Ling Electronics, Inc. This device is capable of operating in the range of 12 kHz and has a relatively large displacement, on the order of 0.20 inch. This particular device is capable of producing all of the required waveforms for touch and vibrotaction measurements.

Continuing to refer to FIG. 3, the components which carry out the pinprick stimulation include a constant torque motor 152 which does not require external electronic feedback control. It is preferred that the constant torque motor 152 be one available from Litton Systems, Inc. and described as a TD-1500-c-1 toroidal motor. The constant torque motor 152 has a shaft 154 to which is attached an arm 158 which is retracted by a spring 156.

A linkage, generally designated at 160, connects a pin receptacle 162 to the arm 158. As shown in the cross sectional view of FIG. 4, the pin receptacle 162 has a hollow end into which a pointed object, such as a hypodermic needle 166, can be inserted. The hypodermic needle 166 is preferably a sterile 20 or 22 gauge hypodermic needle.

Figure 4:
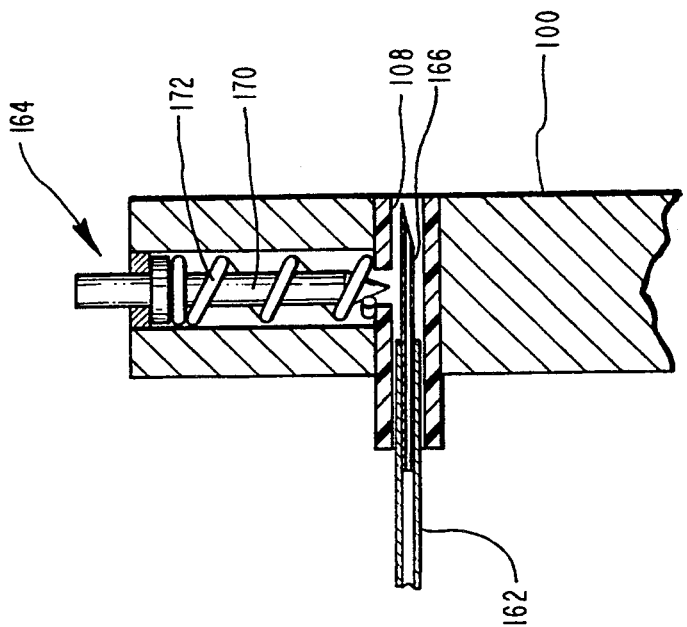
FIG. 4 is a perspective view of the pinprick stimulus components taken along line 4—4 of FIG. 3.

A locking mechanism, generally designated at 164, is provided to facilitate insertion of a new hypodermic needle 166 for each new patient. The locking mechanism 164 includes a shaft 170 which the user can press into the side of the pin receptacle 162 after utilizing a software command directing that the pin receptacle 162 be extended through a guide 168 as shown in FIG. 4. After the hypodermic needle 166 has been installed, the user releases the shaft 170 which is biased out of the way by spring 172.

Referring again to FIG. 3, during operation of the components which carry out the pinprick stimulation, a command signal sets the voltage applied to the constant torque motor 152, which in turn determines the torque (i.e., indentation force) produced by the constant torque motor 152. The maximum indentation force the system described herein can produce is 0.49N (50 g-force), and its range of travel is restricted to 3 mm. A spring 156 returns the pin receptacle 162 to its rest (fully retracted) position when the stimulus is terminated. The spring 156 and the position of the arm 158 linking the motor shaft 154 to the pin receptacle 162 are designed so that the target force is generated at the point of first contact with the skin and falls as the displacement is increased, providing a form of negative feedback which limits skin penetration.

Figure 5:
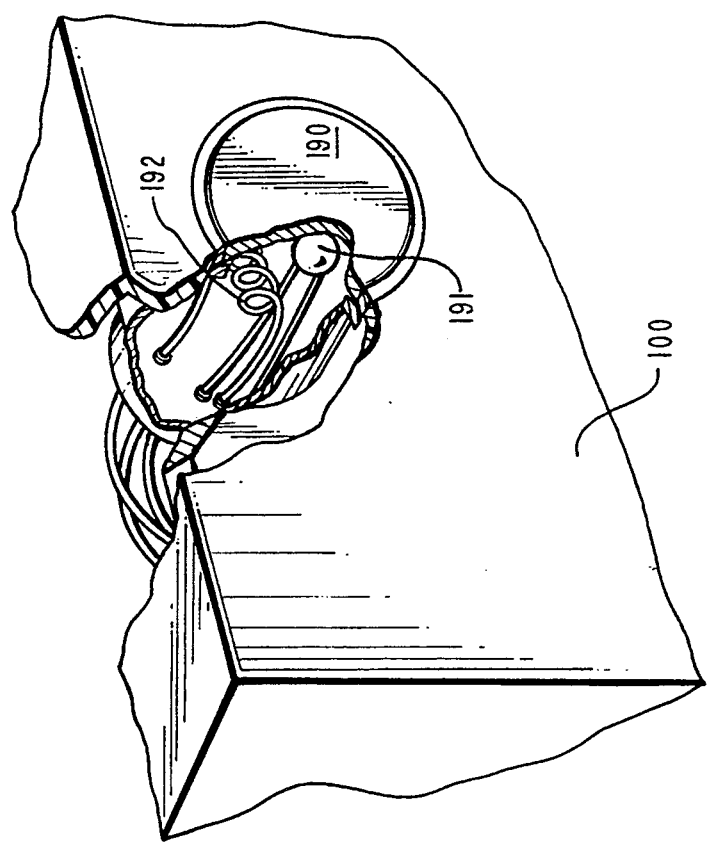
FIG. 5 is a partially cut away perspective view of the temperature stimulus device taken along line 5—5 of FIG. 3.

Continuing to refer to FIG. 3, the components which carry out thermal stimulation include an aluminum disk (shown best in FIG. 5 at 190), which is about 1 centimeter in diameter, which is heated by a resistance coil represented at 192. A thermistor 191 is placed in contact with the aluminum disk. The resistance coil 192 is heated by a servo system in which the digital to analog output from the parallel expansion board 16 sets the desired temperature, and the current flow to the resistance coil 192 is modulated by the difference between the control voltage and the voltage from a thermistor circuit.

For thermal sensory tests, the maximum command temperature is 44.0° C. In the presently preferred embodiments, the temperature of the stimulation is increased at a rate of 4.5° C./second. In other embodiments, the mass of the aluminum disk 190 may be reduced to increase the heating rate. A proportional feedback controller is included in the control module (and is represented in the schematic diagrams included in later figures) which prevents overshoot during step changes in command temperature, and the non-linear (logarithmic) properties of the thermistor 191 are compensated for in the operating code when calculating the proper digital to analog output voltage for a desired temperature.

The maximum available power directed to the resistance coil 192 is 10 watts in the described embodiment, providing a measure of safety in the event of component failure. In some embodiments of the present invention the upper limit on the temperature imposed during thermal stimulation can be increased to provide for testing of nociception with thermal stimuli.

Figure 6:
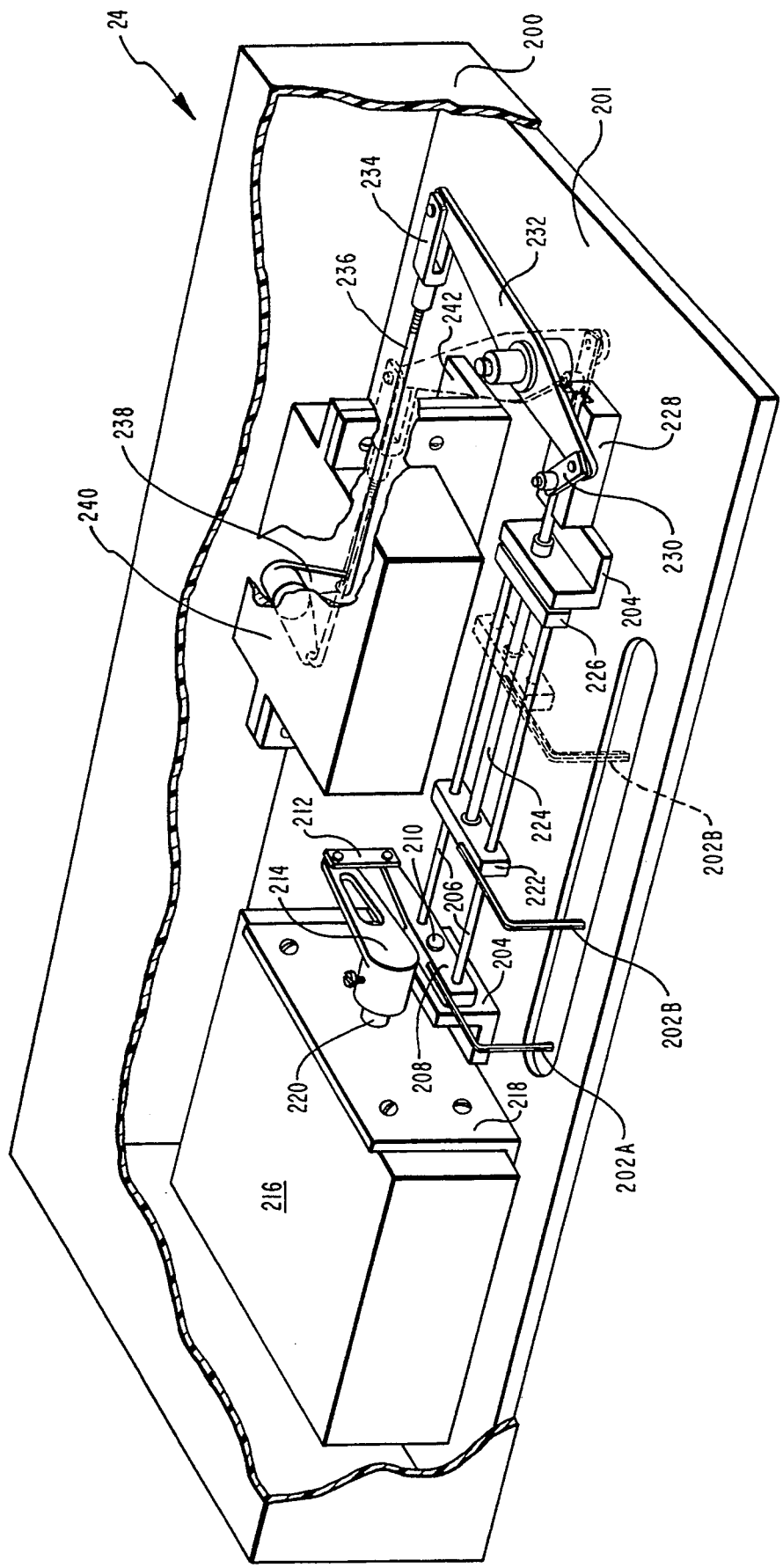
FIG. 6 is a partially cut away perspective view of another stimulation module of the presently preferred system of the present invention which includes the two point discrimination components.

Referring next to FIG. 6, a partially cut away perspective view is provided of the second stimulation module 24. The second stimulation module contains the components which carry out the two point discrimination stimulus of the present invention. The second stimulation module 24 includes a base 201 and a housing 200 in which a servo motor 240 and a galvanometer 216 are contained. The galvanometer 216 is also preferably obtained from General Scanning Inc. model GVM620. The servo motor is preferably one available from Futaba Denshi Kogyo Kabushiki Kaisha, Chiba-Ken, Japan and designated as a FP-S28 servo.

Still referring to FIG. 6, the shaft of the servo motor 240 (which is secured to a base 201 by a bracket 242) is connected to an arm 238 which pulls and pushes a rod 236 which terminates in a clevis 234. The clevis 234 is connected to one end of a pivoting lever 232. The other end of the pivoting lever 232 is provided with a short pivoting arm 230 which is pivotally attached to a positioning rod 224.

As the servo motor 238 operates, the positioning rod 224 slides on guide block 228 to move a rocking member 222 to a different position along a pair of guide rods 206. In FIG. 6 one possible position of the movable structures is shown in solid image while another possible position is shown in phantom image. In the described manner, the distance between the first indentation rod 202A and the second indentation rod 202B can be varied to determine a patient's two point discrimination threshold.

The structure illustrated in FIG. 6 is not only able to impose two variably spaced points upon the skin of the patient but is also able to vary the pressure imposed upon the patient and also modulate (vibrate) the pressure imposed. As illustrated in FIG. 6, the guide rods 206 are held in place at their ends by a rocking holder 226 (pivotally connected to bracket 204) on one of their ends and by a lever holder 210. The lever holder 210 is connected to bracket 204 by pivot 210. As shown in FIG. 6, one indentation rod 202A is connected to the lever holder 210.

As the galvanometer 216 (which is held in place by bracket 218) operates, the galvanometer shaft 220 rotates causing an arm 214 to move through an arc of travel. As the arm 214 travels, an interconnecting member 212 (which is pivotally connected to the end of arm 214 and to the end of lever holder 210) transfers the action of the galvanometer 216 to the indentation rods 202A and 202B. When activated, the indentation rods 202A and 202B extend out from a slot formed in the base 201 of the second stimulation module 24 to contact the skin of the patient.

Thus, it will be appreciated that the components contained within the second stimulation module 24 are able to impose two point discrimination stimulation while also varying the force applied to the patient's skin. Moreover, the galvanometer 216 allows vibrotaction stimulation to be imposed upon the patient combined with the two point discrimination stimulus.

As has been discussed above, various other modules can also be added, including module 26 illustrated in FIG. 1. In one embodiment of module 26, the device is provided with the capability of applying constant current stimulation to the patient. With such a module it is possible to electrically activate the patient's nerve fibers and to obtain further measurements concerning nerve function. In order to acquire accurate data concerning nerve function it may be desirable to include a further monitor 30 which is attached directly to the patient. The monitor 30 may, for example, comprise a device for measuring electrical potentials carried by the patient's nerves.

In operation, a constant current stimulus can be applied by module 26. The result of that stimulus is then measured directly by means of the monitor 30. Some of the measurements which are possible by this mechanism include conduction velocity through the subject nerves, threshold current levels, types of sensations evoked, magnitude of sensation versus magnitude of stimulus (i.e., does-response), and delay time from stimulus until sensation is evoked.

In one such procedure, a cuff electrode is placed over the finger in order to provide an electrical stimulus to the finger. The action potentials evoked are then measured through the skin of the forearm, using monitor 30. Using this type of procedure it is possible to measure slowing of conduction velocity of the type characteristic of motion disorders, such as carpal tunnel syndrome.

In typical operation, the constant current generator which forms a part of module 26 is isolated from the ground. Two probes extend from the current generator and are placed in communication with the skin of the patient. The current then passes through the nerve fibers and the response is measured as discussed above.

Various experimental protocols can be run using this type of device. For example, using one technique, current is repeatedly applied and the evoked action potentials measured. By repeating the procedure the signal is separated from the noise. Thus, by measuring the distance between the stimulating and recording electrodes, and by knowing the time delay between electrical stimulation and recording, it is possible to calculate conduction velocity.

Provided in FIGS. 7–15 are detailed diagrams showing the organization of the certain of the electrical components of the described preferred embodiments. It will be understood that the arrangement of the components illustrated in FIGS. 7–15 are merely exemplary of the many alternative embodiments of the present invention.

Figure 7:
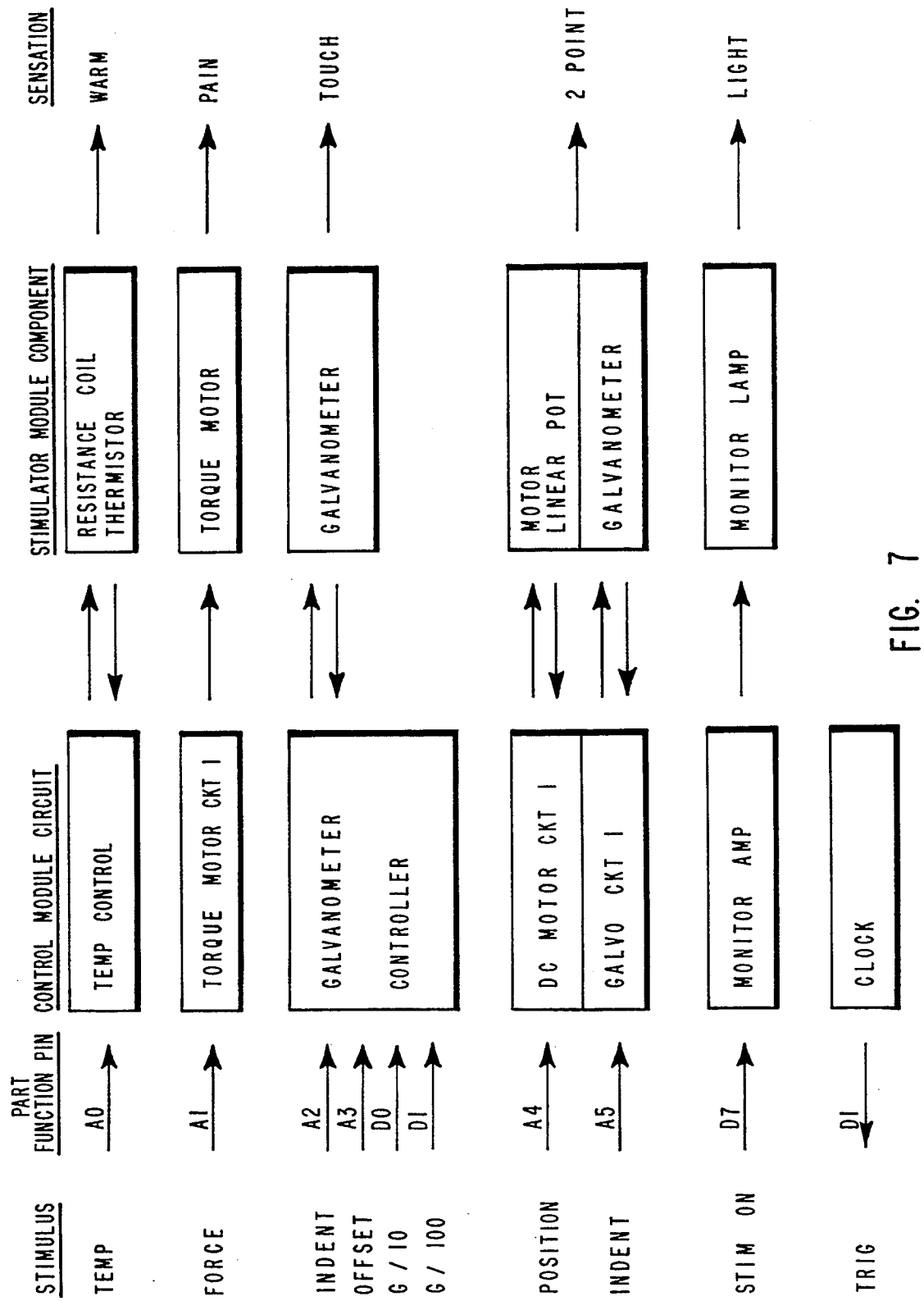
FIG. 7 is a high level block diagram showing the interconnection of some of the principle electrical components of one embodiment of the system of the present invention.

FIG. 7 provides a block diagram of the organization of the electrical components of a portion of the described embodiment. The block diagram of FIG. 7 indicates the stimulus to be imposed upon the patient, the parallel expansion board port assignment, the control module circuit, the stimulation module components, and the sensation to be elicited from the patient.

Figure 8:
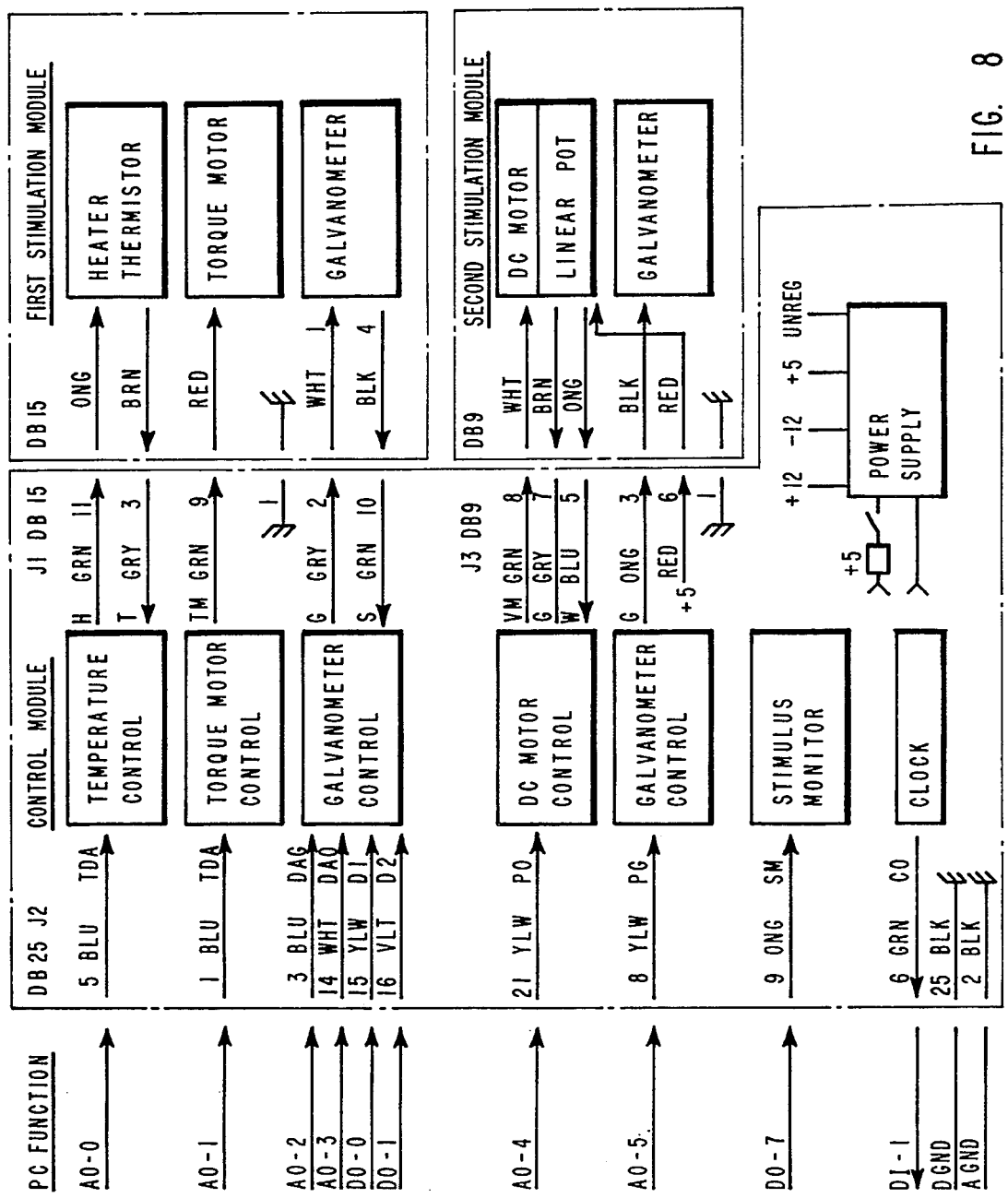
FIGS. 8–15 are detailed diagrams showing the organization of certain electrical components of the presently preferred system of the present invention.

FIG. 8 is a more detailed block diagram showing the organization of the electrical components of the embodiment shown in FIG. 7. The block diagram of FIG. 8 shows the specific pin assignments of various connectors as well as color coding of various leads as they appear on off-the-shelf components and as preferred for interconnecting wiring.

Figure 9:
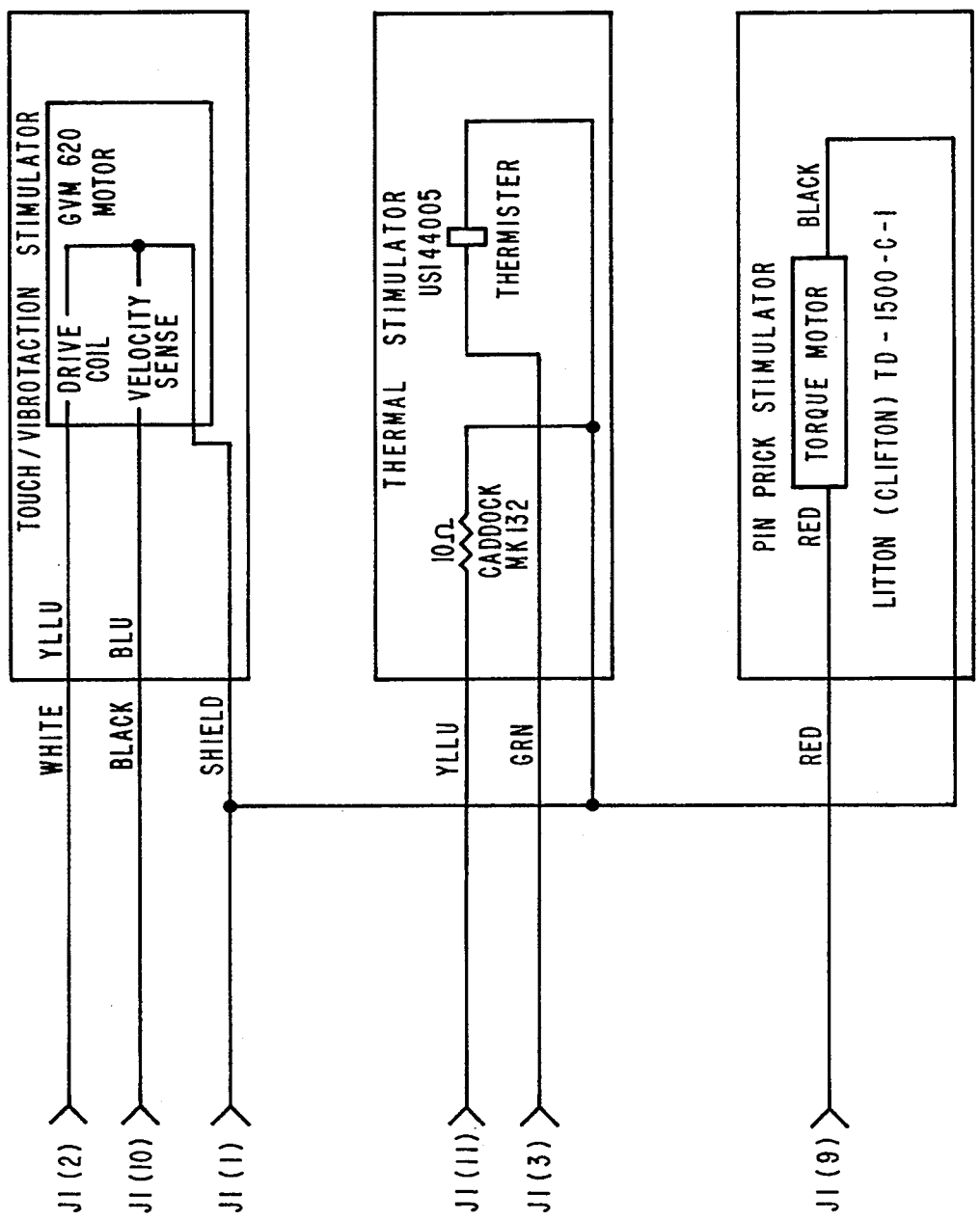

FIG. 9 is an electrical schematic of the galvanometer used in one embodiment of the device to impose touch and vibrotaction stimulation, the heating element, and the thermistor used to impose thermal stimulation, as well as the torque motor used to impose pinprick stimulation on a patient.

Figure 10:
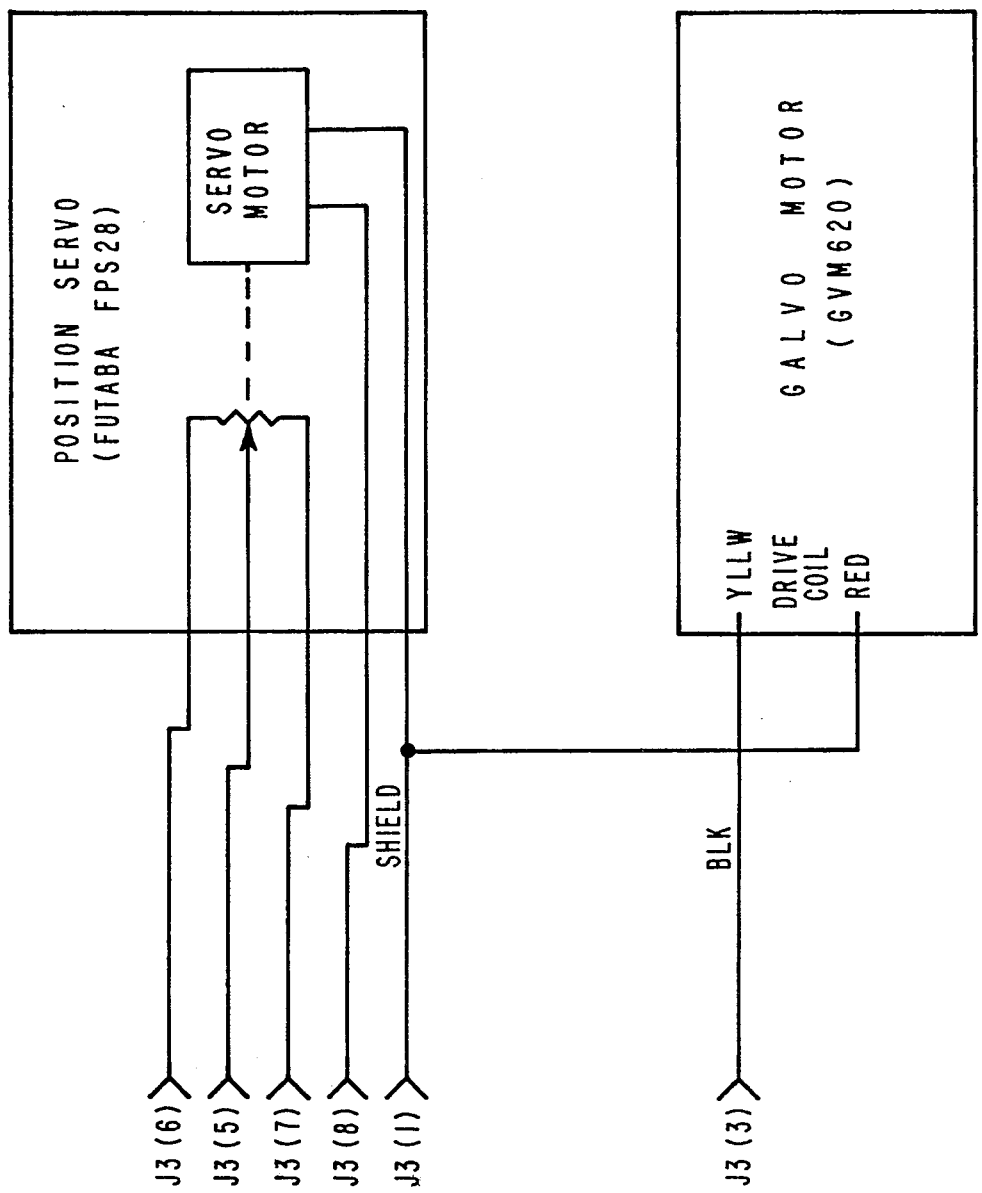

FIG. 10 is an electrical schematic of the galvanometer and servo motor used in one embodiment to impose two point discrimination stimulation on a patient.

Figure 11:
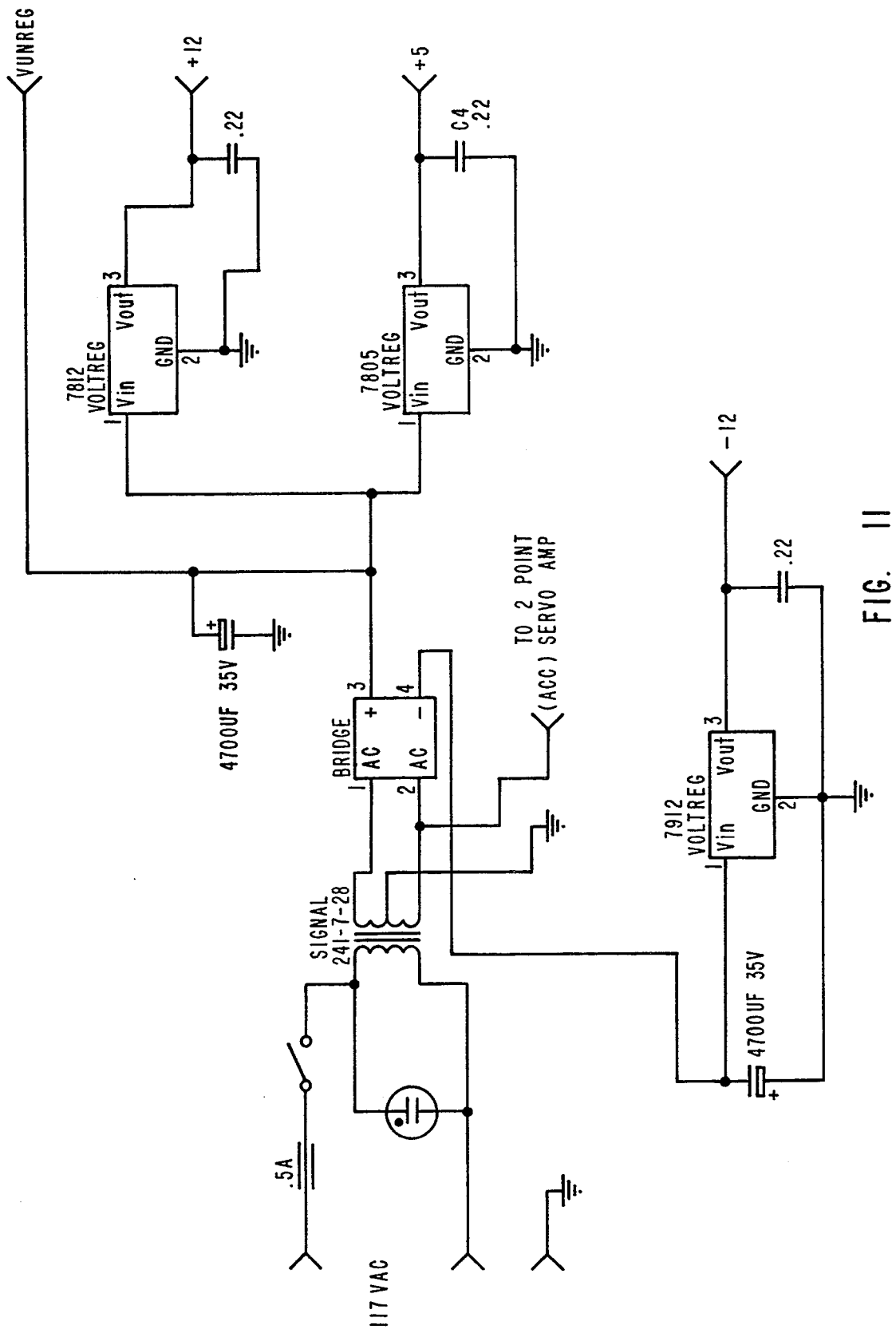

FIG. 11 is a detailed electrical schematic of one embodiment of the power supply circuit included in the control module of the described embodiment.

Figure 12:
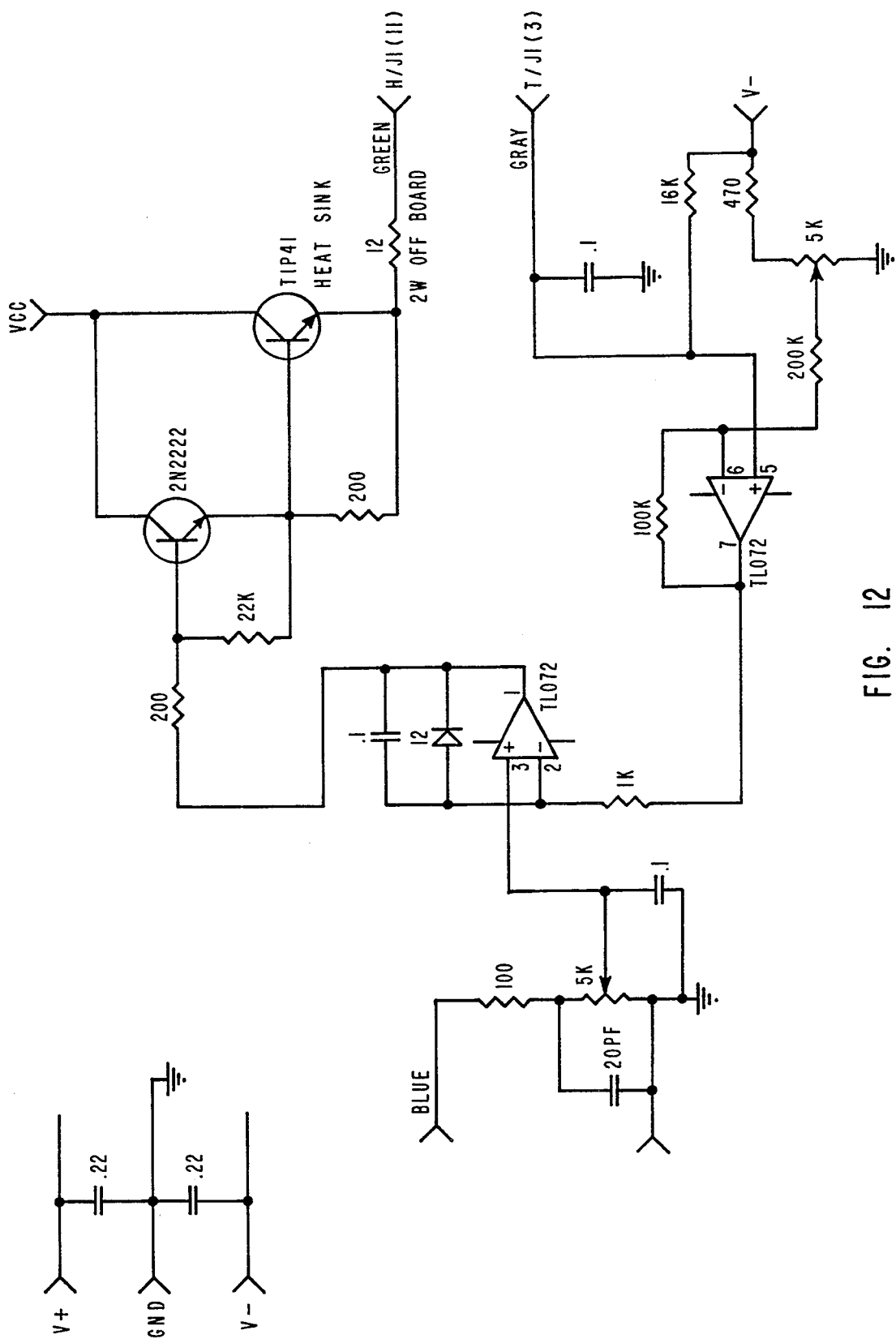

FIG. 12 is a detailed electrical schematic of one embodiment of the temperature control circuit included in the control module of the described embodiment.

Figure 13:
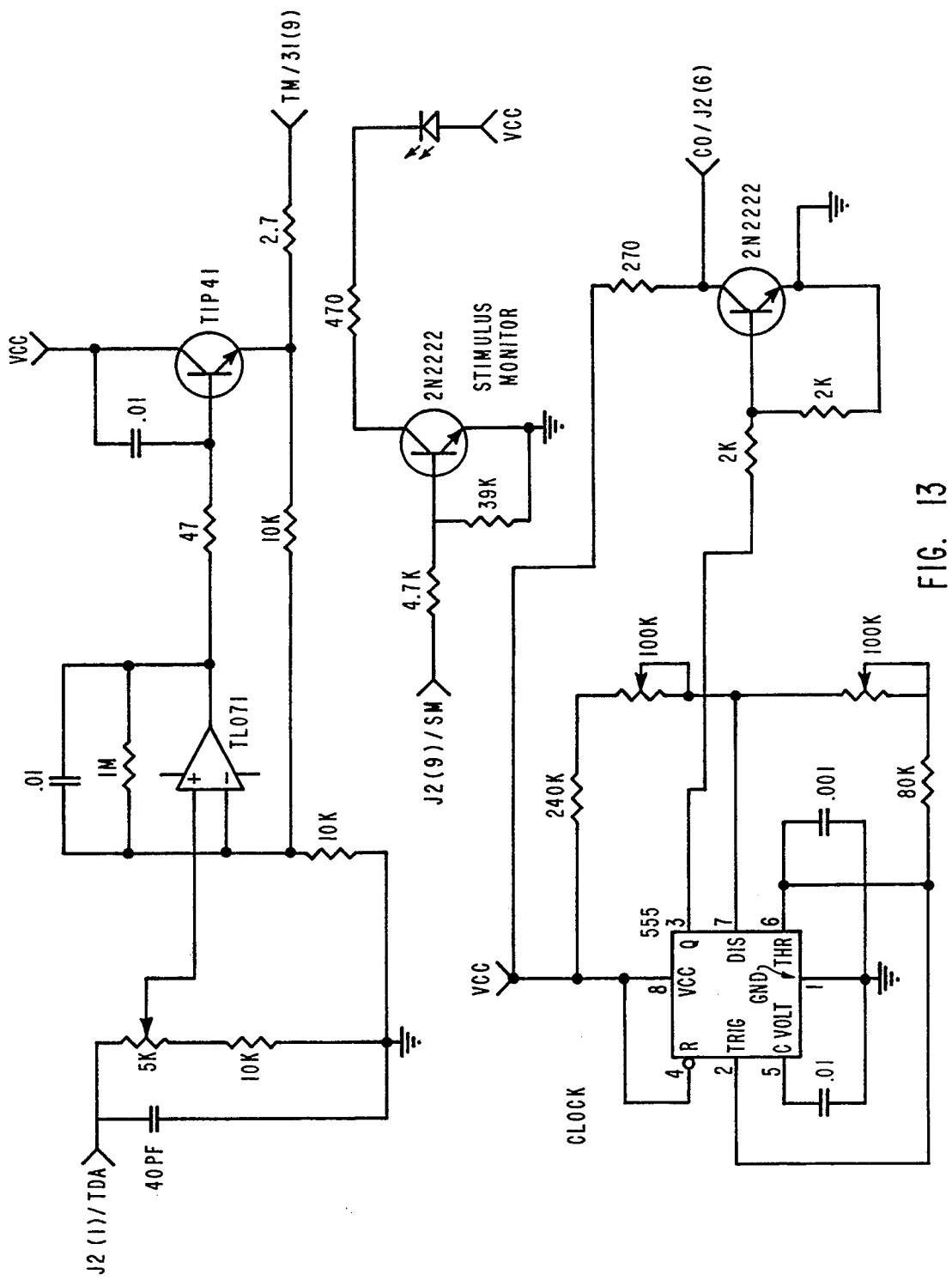

FIG. 13 is a detailed electrical schematic of one embodiment of the torque motor control circuit and clock and stimulus monitor circuits included in the control module of the described embodiment.

Figure 14:
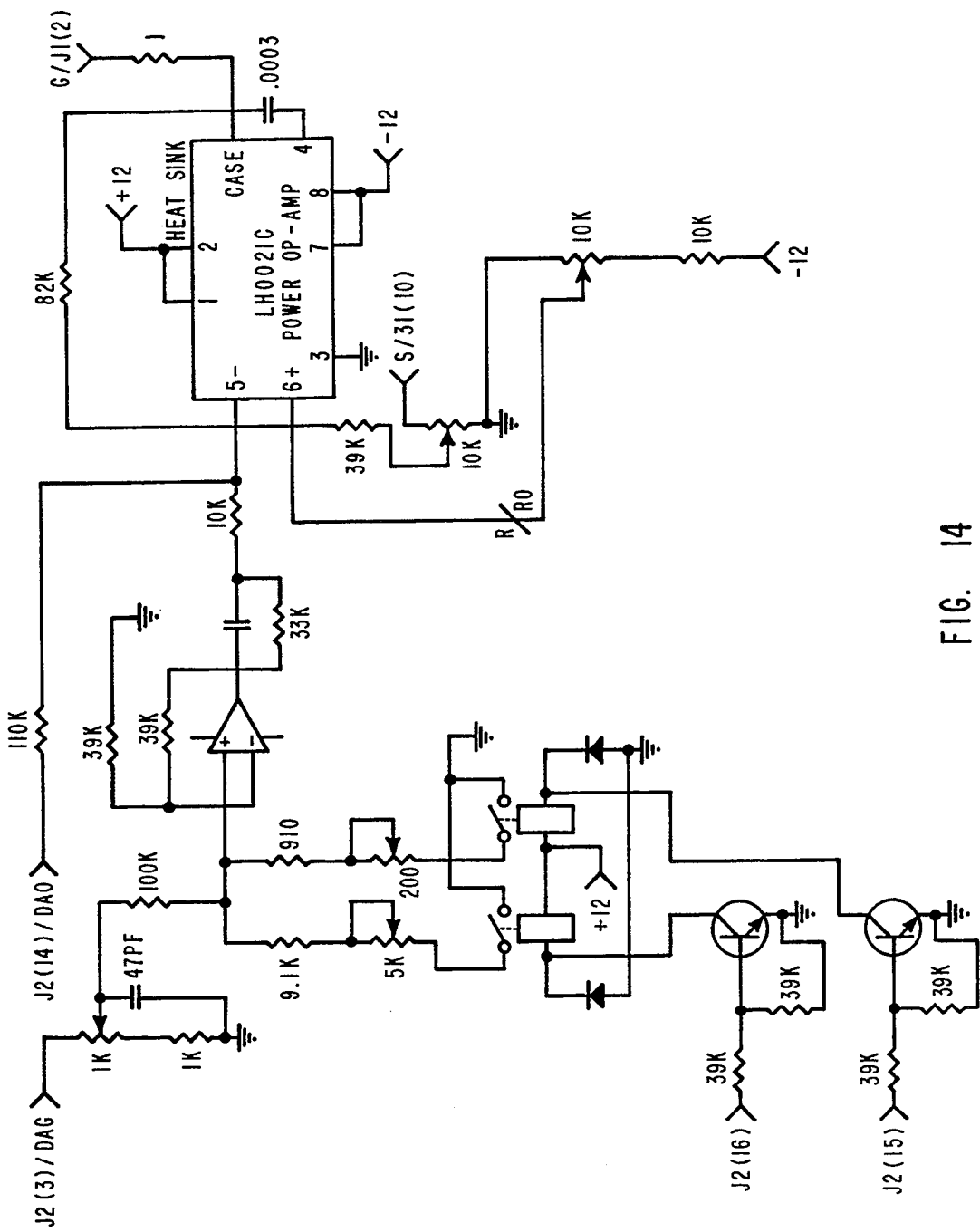

FIG. 14 is a detailed electrical schematic of one embodiment of the galvanometer amplifier circuit included in the control module of the described embodiment.

Figure 15:
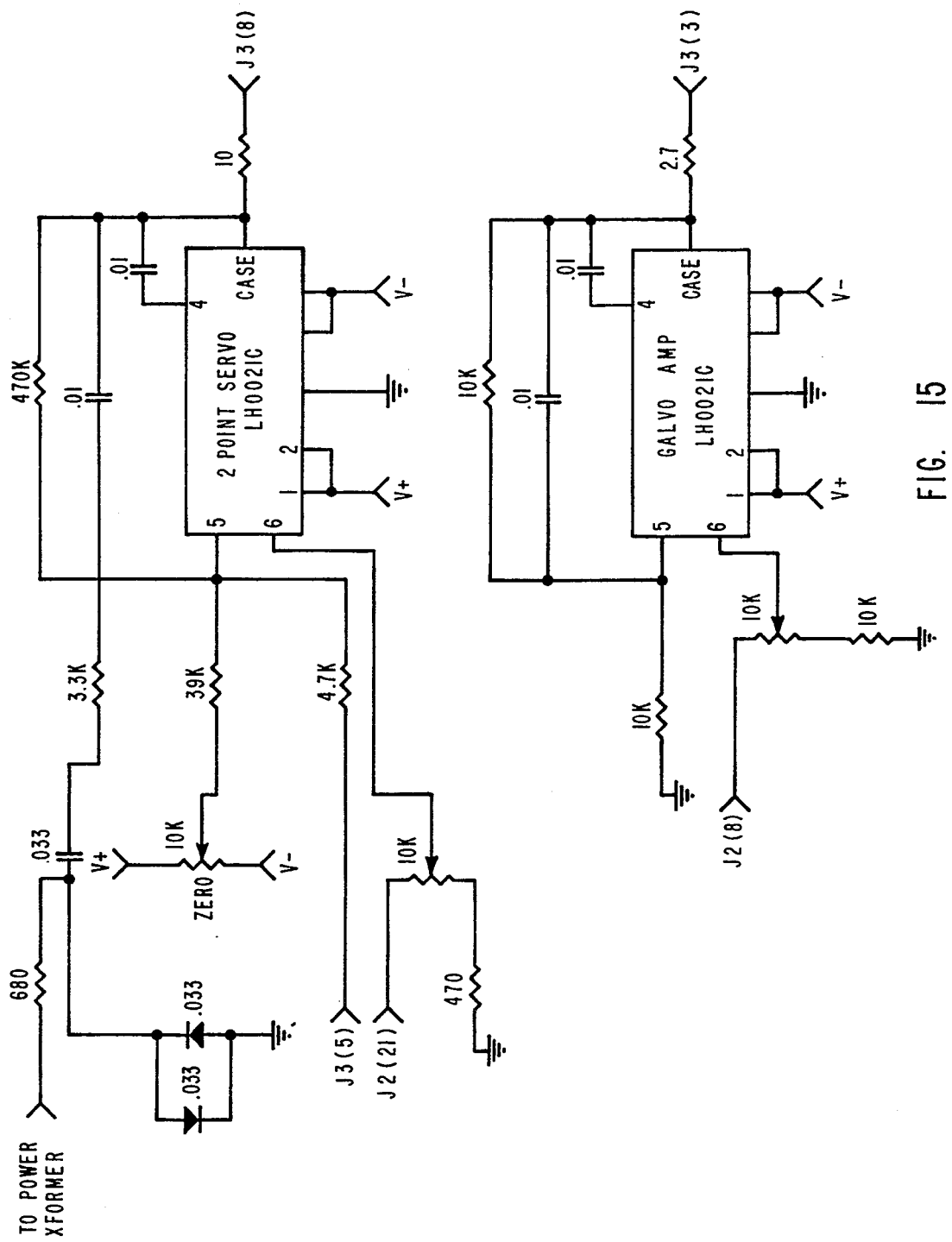

FIG. 15 is a detailed electrical schematic of one embodiment of the galvanometer amplifier and the servo motor amplifier circuits included in the control module of the described embodiment.

From the forgoing, it will be appreciated the present invention provides a great advance over the previously used methods, both manual and any automated methods which are known, of performing tactile testing. Moreover, the present invention provides the advantages of performing a plurality of tests automatically and recording the results automatically.

The present invention is particularly adapted for use in a clinical application but may also be used in analytical or research applications. The tests carried out using the present invention are repeatable and reproducible. For example, the present invention can be used regularly after peripheral nerve repair surgery to document the return of the three major modalities of cutaneous sensation over the recovery period and such testing can be used to assess the success, or lack thereof, of the surgery.

The present invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for automatically testing the cutaneous sensory response of a patient, the apparatus comprising:
   at least one stimulation means for cutaneous stimulation of the patient, said stimulation means comprising means for applying a constant current stimulus;
   control means for accurately controlling the amplitude of stimulus administered by operation of the at least one stimulation means, such that stimuli of precise predetermined amplitude are administered;
   means for receiving direct patient response to the stimulus administered by the stimulation means, said means for receiving direct patient response comprising means for measuring delay between stimulus and sensation;
   means for recording said patient response to the stimuli; and
   computer means for generating additional stimuli in response to the record of the patient response to the stimuli such that a predetermined set of data can be collected.

2. An apparatus for automatically testing the cutaneous sensory response of a patient as defined in claim 1 wherein said means for receiving direct patient response to the stimuli administered by the stimulation means comprises means for the patient to voluntarily indicate sensing the stimuli.

3. An apparatus for automatically testing the cutaneous sensory response of a patient as defined in claim 2 wherein said means for the patient to voluntarily indicate sensing the stimuli comprises a button which can be pressed by the patient.

4. An apparatus for automatically testing the cutaneous sensory response of a patient as defined in claim 2 wherein said means for the patient to voluntarily indicate sensing the stimuli comprises a slide which can be positioned by the patient.

5. An apparatus for automatically testing the cutaneous sensory response of a patient as defined in claim 1 wherein said means for receiving direct patient response to the stimuli administered by the stimulation means comprises means for monitoring physiological change in the patient.

6. An apparatus for automatically testing the cutaneous sensory response of a patient as defined in claim 1 wherein said means for receiving direct patient response to the stimuli administered by the stimulation means comprises means for monitoring electrical change in the patient.

7. An apparatus for automatically testing the cutaneous sensory response of a patient as defined in claim 1 wherein said means for receiving direct patient response to the stimuli administered by the stimulation means comprises means for measuring conduction velocity.

8. An apparatus for automatically testing the cutaneous sensory response of a patient as defined in claim 1 wherein said means for receiving direct patient response to the stimuli administered by the stimulation means comprises means for measuring threshold current.

9. An apparatus for automatically testing the cutaneous sensory response of a patient, the apparatus comprising:
   first stimulation means for cutaneous stimulation of the patient;
   second stimulation means for cutaneous stimulation of the patient;
   control means for accurately controlling the amplitude and time course of stimuli administered by operation of the first stimulation means and the second stimulation means, such that stimuli of precise predetermined amplitude and time course are administered;
   means for receiving direct patient response to the stimulus administered by at least one of the stimulation means, said means for receiving direct patient response comprising means for monitoring physiological change in the patient; and
   computer means for recording the patient response to the first and second stimulation means for cutaneous stimulation of the patient and for generating further stimuli in response to the record of the patient response to the stimuli.

10. An apparatus for automatically testing the cutaneous sensory response of a patient as defined in claim 9 wherein said means for receiving direct patient response to the stimuli administered by at least one of the stimulation means comprises means for the patient to voluntarily indicate sensing the stimuli.

11. An apparatus for automatically testing the cutaneous sensory response of a patient as defined in claim 9 wherein said means for the patient to voluntarily indicate sensing the stimuli comprises a button which can be pressed by the patient.

12. An apparatus for automatically testing the cutaneous sensory response of a patient as defined in claim 9 wherein said means for the patient to voluntarily indicate sensing the stimuli comprises a slide which can be positioned by the patient.

13. An apparatus for automatically testing the cutaneous sensory response of a patient as defined in claim 9 wherein said means for receiving direct patient response to the stimuli administered by at least one of the stimulation means comprises means for monitoring electrical change in the patient.

14. An apparatus for automatically testing the cutaneous sensory response of a patient as defined in claim 9 wherein said first stimulation means for cutaneous stimulation of the patient comprises means for applying a constant current stimulus.

15. An apparatus for automatically testing the cutaneous sensory response of a patient as defined in claim 14 wherein said means for receiving direct patient response to the stimuli administered by at least one of the stimulation means comprises means for measuring conduction velocity.

16. An apparatus for automatically testing the cutaneous sensory response of a patient as defined in claim 14 wherein said means for receiving direct patient response to the stimuli administered by at least one of the stimulation means comprises means for measuring threshold current.

17. An apparatus for automatically testing the cutaneous sensory response of a patient as defined in claim 14 wherein said means for receiving direct patient response to the stimuli administered by at least one of the stimulation means comprises means for measuring delay between stimuli and sensation.

18. An apparatus for automatically testing the tactile sensory response of a patient, the apparatus comprising:
   first tactile stimulation means for cutaneous stimulation of the patient;
   second tactile stimulation means for cutaneous stimulation of the patient;
   control means for accurately controlling the amplitude and time course of stimuli administered by operation of the first tactile stimulation means and the second tactile stimulation means such that stimuli of precise predetermined amplitude and time course are administered;
   means for receiving direct patient response to the stimuli administered by at least one of the stimulation means; and
   computer means for recording the patient's responses to said first and the second tactile stimulation means for cutaneous stimulation of the patient and for generating additional stimuli in response to the record of the patient's response to said stimuli.

19. An apparatus for automatically testing the tactile sensory response of a patient as defined in claim 18, wherein said first tactile stimulation means for cutaneous stimulation of the patient comprises a temperature means for applying a nonambient temperature to the patient's skin.

20. An apparatus for automatically testing the tactile sensory response of a patient as defined in claim 18, wherein said first tactile stimulation means for cutaneous stimulation of the patient comprises a pinprick means for pricking the patient's skin.

21. An apparatus for automatically testing the tactile sensory response of a patient as defined in claim 18, wherein said first tactile stimulation means for cutaneous stimulation of the patient comprises an indentation means for indenting the patient's skin.

22. An apparatus for automatically testing the tactile sensory response of a patient as defined in claim 18, wherein said first tactile stimulation means for cutaneous stimulation of the patient comprises a vibration means for vibrating the patient's skin.

23. An apparatus for automatically testing the tactile sensory response of a patient as defined in claim 18, wherein said first tactile stimulation means for cutaneous stimulation of the patient comprises a touch discrimination means for making two spaced apart contacts with the patient's skin.

24. An automatic testing apparatus comprising:
   a tactile stimulation means for applying stimuli to the patient's skin;
   control means for accurately controlling the amplitude of the stimuli administered by said tactile stimulation means such that stimuli of precise predetermined amplitude are administered;
   means for receiving direct patient response to the stimuli administered by the tactile stimulation means;
   means for recording said patient response to the stimuli; and
   computer means for generating additional stimuli in response to the record of the patient response to the stimuli such that a predetermined set of data can be collected,
   wherein said automatic testing apparatus is capable of automatically testing the cutaneous sensory response of a patient by automatically testing a principal modality of cutaneous sensation, said tactile stimulation means comprises temperature means for applying a nonambient temperature to the patient's skin, and said automatic testing apparatus is capable of automatically testing the cutaneous sensory response of a patient by automatically testing the temperature modality of cutaneous sensation.

25. The automatic testing apparatus as defined in claim 24, wherein said tactile stimulation means comprises vibration means for vibrating the patient's skin, said automatic testing apparatus capable of automatically testing the cutaneous sensory response of a patient by automatically testing the touch modality of cutaneous sensation.

26. The automatic testing apparatus as defined in claim 24, wherein said tactile stimulation means comprises constant current means for applying a constant current to the patient's skin, said automatic testing apparatus capable of automatically testing the cutaneous sensory response of a patient by automatically testing the touch modality of cutaneous sensation.

27. An automatic testing apparatus comprising:
   a tactile stimulation means for applying stimuli to the patient's skin;
   control means for accurately controlling the amplitude of the stimuli administered by said tactile stimulation means such that stimuli of precise predetermined amplitude are administered;
   means for receiving direct patient response to the stimuli administered by the tactile stimulation means;
   means for recording said patient response to the stimuli; and
   computer means for generating additional stimuli in response to the record of the patient response to the stimuli such that a predetermined set of data can be collected,
   wherein said automatic testing apparatus is capable of automatically testing the cutaneous sensory response of a patient by automatically testing a principal modality of cutaneous sensation, wherein said tactile stimulation means comprises pinprick means for pricking the patient's skin, and said automatic testing apparatus incapable of automatically testing the cutaneous sensory response of a patient by automatically testing the pain modality of cutaneous sensation.

28. An automatic testing apparatus comprising:
   a tactile stimulation means for applying stimuli to the patient'skin;
   control means for accurately controlling the amplitude of the stimuli administered by said tactile stimulation means such that stimuli of precise predetermined amplitude are administered;
   means for receiving direct patient response to the stimuli administered by the tactile stimulation means;

means for recording said patient response to the stimuli; and computer means for generating additional stimuli in response to the record of the patient response to the stimuli such that a predetermined set of data can be collected, wherein said automatic testing apparatus is capable of automatically testing the cutaneous sensory response of a patient by automatically testing a principal modality of cutaneous sensation, wherein said tactile stimulation means comprises indentation means for indenting the patient's skin, and said automatic testing apparatus is capable of automatically testing the cutaneous sensory response of a patient by automatically testing the touch modality of cutaneous sensation.

29. An automatic testing apparatus comprising:

a tactile stimulation means for applying stimuli to the patient's skin;

control means for accurately controlling the amplitude of the stimuli administered by said tactile stimulation means such that stimuli of precise predetermined amplitude are administered;

means for receiving direct patient response to the stimuli administered by the tactile stimulation means;

means for recording said patient response to the stimuli; and computer means for generating additional stimuli in response to the record of the patient response to the stimuli such that a predetermined set of data can be collected, wherein said automatic testing apparatus is capable of automatically testing the cutaneous sensory response of a patient by automatically testing a principal modality of cutaneous sensation, wherein said tactile stimulation means comprises touch discrimination means for making two spaced apart contacts with the patient's skin, and said automatic testing apparatus is capable of automatically testing the cutaneous sensory response of a patient by automatically testing the touch modality of cutaneous sensation.

* * * * *